(12) United States Patent
Takehara (10) Patent No.: US 8,566,120 B2
(45) Date of Patent: Oct. 22, 2013

(54) HEALTH DATA GENERATING METHOD, HEALTH DATA GENERATION APPARATUS THEREFOR, USER TERMINAL THEREFOR, AND COMPUTER-READABLE RECORDING MEDIUM THEREFOR

(75) Inventor: Katsumi Takehara, Tokyo (JP)

(73) Assignee: Tanita Corporation, Tokyo (JP)

( * ) Notice: Subject to any disclaimer, the term of this patent is extended or adjusted under 35 U.S.C. 154(b) by 1407 days.

(21) Appl. No.: 11/957,145

(22) Filed: Dec. 14, 2007

(65) Prior Publication Data

US 2008/0154645 A1 Jun. 26, 2008

(30) Foreign Application Priority Data

Dec. 25, 2006 (JP) ................................ 2006-348149

(51) Int. Cl.
*G06Q 50/00* (2012.01)
(52) U.S. Cl.
USPC ............. 705/3; 600/300; 600/547; 600/587; 702/19
(58) Field of Classification Search
USPC ............. 705/2–4; 600/300, 547, 587; 702/19
See application file for complete search history.

(56) References Cited

U.S. PATENT DOCUMENTS

| | | | | |
|---|---|---|---|---|
| 6,354,996 | B1 | 3/2002 | Drinan et al. | 600/300 |
| 6,454,708 | B1 | 9/2002 | Ferguson et al. | 600/300 |
| 6,539,310 | B2 * | 3/2003 | Shimomura | 702/19 |
| 6,685,654 | B2 * | 2/2004 | Yoshimura et al. | 600/587 |
| 6,734,856 | B2 * | 5/2004 | Ishikawa et al. | 345/440 |
| 7,024,369 | B1 * | 4/2006 | Brown et al. | 705/2 |
| 7,764,991 | B2 * | 7/2010 | Yamazaki et al. | 600/547 |
| 2002/0055419 | A1 * | 5/2002 | Hinnebusch | 482/8 |
| 2004/0117212 | A1 * | 6/2004 | Kong et al. | 705/2 |
| 2004/0122297 | A1 | 6/2004 | Stahmann et al. | 600/300 |
| 2005/0071197 | A1 | 3/2005 | Goldberg | 705/2 |
| 2006/0292039 | A1 * | 12/2006 | Iida | 422/82.05 |

FOREIGN PATENT DOCUMENTS

| | | |
|---|---|---|
| EP | 1 070 479 A2 | 1/2001 |
| EP | 1 421 896 A2 | 5/2004 |
| JP | 2003-235834 | 8/2003 |
| JP | 2003-288417 | 10/2003 |

(Continued)

OTHER PUBLICATIONS

Zimmerman, C. L. (1999). A network interpretation approach to the balance scale task. (Order No. NQ46955, University of Alberta (Canada)). ProQuest Dissertations and Theses, 181-181 p. Retrieved from http://search.proquest.com/docview/304547938?accountid=14753. (304547938).*
European Search Report dated Apr. 18, 2008, corresponding to European Application No. EP07023653.

(Continued)

*Primary Examiner* — Mark Holcomb
(74) *Attorney, Agent, or Firm* — Hogan Lovells US LLP (57) ABSTRACT

A health data generation system has a measuring apparatus and a user terminal. The measuring apparatus transmits to the user terminal function type information indicating function of the measuring apparatus. The user terminal selects a desired function based on the received function type information and transmits the selected function as function designation information to measuring apparatus. The measuring apparatus transmits to the user terminal parameter specifying information designating the types of parameters necessary for performing the function specified by the function designation information. The user terminal prompts a user to input individual data to the parameters and registers the individual data together with the function designation information as registration information R.

14 Claims, 8 Drawing Sheets

(56) References Cited

FOREIGN PATENT DOCUMENTS

| | | |
|---|---|---|
| JP | 2003-310566 | 11/2003 |
| JP | 2004-013508 | 1/2004 |
| JP | 2006325921 | 12/2007 |
| WO | WO 2006/120600 A1 | 11/2006 |

OTHER PUBLICATIONS

European Office Action Issued May 19, 2009.
Notice of Allowance from JPO, Japanese Patent Application No. 2006-348149, Issue Date Apr. 3, 2012.

* cited by examiner

| FUNCTION TYPE INFORMATION | PARAMETER SPECIFYING INFORMAITON |
|---|---|
| WEIGHT SCALE | NONE |
| BODY FAT PERCENTAGE MEASURING DEVICE | HEIGHT, SEX |
| BODY COMPOSITION MEASURING DEVICE | HIGHT, SEX, AGE, INDICES TO BE MEASURED |

TBL

THE MEASURING DEVICE HAS THE FOLLOWING FUNCTIONS. PLEASE SELECT A FUNCTION YOU WISH TO USE.
- ◎ WEIGHT SCALE
- ◎ BODY FAT PERCENTAGE MEASURING DEVICE
- ● BODY COMPOSITION MEASURING DEVICE

FIG. 9B

PARAMETER INPUT SCREEN

·PLEASE ENTER YOUR HEIGHT.
   [ 170 ] CM

·PLEASE ENTER YOUR AGE.
   [ 35 ] YEARS OLD

·PLEASE USE YOUR SEX.
   ● MALE    ◎ FEMALE

·PLEASE SELECT INDICES YOU WISH TO HAVE MEASURED.
   ◎ BODY WATER MASS   ● VISCERAL FAT CROSS-SECTIONAL AREA
   ◎ BONE MASS   ● BASAL METABOLISM   ● MUSCLE MASS

L1 (REGISTER)

FIG. 9C

HEALTH DATA GENERATING METHOD, HEALTH DATA GENERATION APPARATUS THEREFOR, USER TERMINAL THEREFOR, AND COMPUTER-READABLE RECORDING MEDIUM THEREFOR

BACKGROUND OF THE INVENTION

1. Field of the Invention

The present invention relates to a health data generating method for taking measurements of indexes of a human subject and for generating health data useful for healthcare based on the measurements, a health data generation apparatus therefor, a user terminal therefor, and a computer-readable recording medium therefor.

2. Description of Related Art

Health data generation apparatuses have been widely used that are capable of producing data that serves as indexes of health conditions (hereinafter, this will be referred to as "health data") such as body fat percentage and visceral fat cross-sectional area. A health data generation apparatus of this type sometimes has plural functions capable of generating plural types of health data such as body weight, body fat percentage, visceral fat cross-sectional area, body water mass, and bone mass, such as a body composition measuring device described in Japanese Patent Application Laid-Open Publication No. 2006-325921.

The health data includes those which can be directly measured, such as body weight, and those which are generated through computation using an estimation equation such as body fat percentage, visceral fat cross-sectional area, body water mass, or bone mass that cannot be directly measured. In a case in which health data is generated according to an estimation equation, individual data of a human subject such as height, age, and sex are used as parameters, in addition to the human subject measurements, such as body weight and bioelectric impedance, which can be physically measured. However, because those parameters used in the equation vary depending on a function, a user must perform complicated setting and inputting operations even in a case in which the user wishes to obtain only one or a few particular types of human subject indexes. Furthermore, even if a user wishes to use only one function of the plural functions of a multifunctional health data generation apparatus, the user has to select the function for each measurement, which is troublesome for a young person or an elderly person who may often be unfamiliar with the operations of the device.

SUMMARY OF INVENTION

The present invention was made in consideration of the above, and the present invention has as an object to provide a health data generating method according to which the health data which a user wishes to obtain can be generated without requiring cumbersome and complicated operations by the user, and to provide a health data generation apparatus therefor, a user terminal therefor, and a computer-readable recording medium therefor.

To solve the above objects, the present invention provides a health data generating method for use in a health data generation system having a health data generation apparatus and a user terminal capable of communicating with the health data generation apparatus, the user terminal having a storage device for storing predetermined data and the health data generation apparatus having a human subject index measuring device for measuring conditions of a human subject and outputting human subject index information, and having plural functions of generating plural types of health data serving as indices of health conditions, the method including steps of: transmitting, from the user terminal to the health data generation apparatus, a function inquiry for inquiring about functions of the health data generation apparatus; transmitting, from the health data generation apparatus to the user terminal, upon receiving the function inquiry, a function response containing function type information indicating the types of the plural functions; displaying, at the user terminal, the functions of the health data generation apparatus based on the function type information contained in the received function response, thereby prompting a user to designate one of the functions, and transmitting from the user terminal the designated function as the function designation information to the health data generation apparatus; transmitting, from the health data generation apparatus to the user terminal, parameter specifying information specifying types of parameters necessary for generating the health data that will be generated by the function designated by the received function designation information; generating registration information including the function designation information and individual data of the user associated with each other by prompting at the user terminal the user to input the individual data for the types of parameters specified by the received parameter specifying information, the registration information then being stored in the storage device; transmitting, from the user terminal to the health data generation apparatus, an execution request containing the registration information after reading the registration information from the storage device in a case in which an operation input for measuring a health condition is performed by the user; and generating, upon receiving the execution request containing the registration information from the user terminal, health data corresponding to the function designated by the function designation information included in the registration information based on the human subject index information of the user and the individual data included in the registration information.

In the health data generation method according to the present invention, parameters necessary for implementing a function of the health data generation apparatus are stored in the storage device of the user terminal as registration information (function designation information and individual data). A user is then enabled to instruct the measurement of a health condition with a desired function merely by transmitting to the health data generation apparatus registration information after reading the registration information from the user terminal. That is, health data can be generated without requiring cumbersome and complicated operations by the user. Also, only the health data the user wishes to obtain can be generated with simple operations. Thus, the convenience to the user is improved.

In a preferred embodiment, in a case in which the user terminal is used by plural users, and in which the storage device stores plural sets of the registration information generated for each of the plural users, the step of generating registration information includes: prompting the user to input call name information for uniquely specifying the user; and generating a nickname including the function designation information and the call name information and storing the nickname in association with the function designation information and with the individual data as the registration information; and the step of transmitting the execution request includes: displaying plural nicknames; prompting the user to select one of the plural nicknames; reading, from the storage device, as the registration information, the function designation information and the individual data corresponding to the nickname selected by the user; and transmitting the execution request containing the registration information.

A health data generation apparatus may often be shared by plural users, such as the members of a family. According to the health data generation method of the present invention, because a nickname consisting of function designation information and call name information of a user is assigned to each of the plural pairs of individual data and function designation information and is stored as registration information together with a pair of individual data and function designation information, a user only has to select a desired nickname at the user terminal and causes the user terminal to transmit a measurement request to the health data generation apparatus, whereby a user can readily use a desired function of the health data generation apparatus. Furthermore, the convenience of the user is improved compared with a configuration in which plural individual keys are provided at the body of a health data generation apparatus and in which individual data used for the generation of health data is stored in association with each individual key, because the user no longer has to remember which individual key is associated with the individual data of the user.

In another preferred embodiment, in a case in which at least one of the plural sets of health data is generated based only on the human subject index information, the step of transmitting parameter specifying information includes, in a case in which there is parameter specifying information corresponding to the received function designation information, transmitting the corresponding parameter specifying information, whereas, in a case in which the function designated by the function designation information is for generating health data based only on the human subject index information and in which there is no parameter specifying information corresponding to the received function designation information, notifying the user terminal to that effect; and the step of registering the registration information includes the function designation information as the registration information in a case in which the user terminal receives a notification that there is no parameter specifying information corresponding to the function designation information.

The health data generation apparatus is sometimes provided with a function of generating health data only based on human subject index information (for example, a body weight measuring function, i.e., a weight scale). Because no parameters are used for such a function, parameter specifying information need not be transmitted from the health data generation apparatus to the user terminal. Therefore, in the present invention, in a case in which there is no parameter specifying information corresponding to a function designated by the received function designation information, the health data generation apparatus notifies a user to that effect. In this case, the user terminal stores only the function designation information as registration information. According to this embodiment, any function of the health data generation apparatus can be registered as registration information regardless of whether there is parameter specifying information corresponding to the function. Therefore, a user is able to specify any desired function of the health data generation apparatus through the user terminal.

The present invention further provides a health data generation apparatus provided with plural functions for generating plural types of health data serving as indices of health conditions and capable of communicating with a user terminal operated by a user, the health data generation apparatus having: a human subject index measurer for measuring conditions of a human subject and outputting human subject index information; a function storage device for storing function type information indicating types of the plural functions and parameter specifying information specifying types of parameters relating to characteristics of the human subject, the parameters being used for the generation of a particular type of the health data corresponding to the function type; a function responder for, upon receiving a function inquiry for inquiring about a function of the health data generation apparatus, referring to the function storage device and transmitting a function response to the user terminal the function response containing the function type information for the plural types of functions; a parameter responder for, upon receiving function designation information for designating a type of function of the health data generation apparatus, reading from the function storage device, the parameter specifying information corresponding to the function designated in the function designation information and for transmitting a parameter response containing the parameter specifying information to the user terminal; and a health data generator for, upon receiving from the user terminal an execution request containing registration information that includes the function designation information and individual data, with the execution request instructing generation of health data corresponding to the function designated by the function designation information and with the individual data corresponding to the parameter specifying information, generating the health data by executing a predetermined computation based on the human subject index information measured by the human subject index measuring device and the individual data included in the registration information.

The health data generation apparatus according to the present invention transmits, in response to a request from a user terminal, function type information indicating the types of functions of the health data generation apparatus to the user terminal. Furthermore, in a case in which function designation information designating one of the functions is received from the user terminal, the health data generation apparatus transmits, to the user terminal, information specifying parameters necessary for implementing the function as parameter specifying information. With this configuration, the user terminal is enabled to store, in a storage device, registration information (a pair of function designation information and individual data) relating to the health data generation apparatus. Therefore, a user only has to read the registration information from the user terminal for transmission to the health data generation apparatus, to instruct the health data generation apparatus to measure a health condition with a desired function. That is, only the health data a user wishes to obtain can be generated without requiring cumbersome and complicated operations by the user. Thus, the convenience to the user is improved.

Furthermore, the present invention provides a user terminal operated by a user and capable of communicating with a health data generation apparatus having plural functions for generating plural types of health data serving as indices of health conditions, the user terminal having: storage device for storing predetermined information; a function requester for transmitting, to the health data generation apparatus, a function inquiry for inquiring about functions of the health data generation apparatus; a function designation requester for, upon receiving from the health data generation apparatus, a function response containing function type information indicating types of the plural functions, displaying the functions of the health data generation apparatus based on the types of functions indicated by the function type information, the display prompting the user to designate one of the functions, and for transmitting a function designation request containing function designation information indicating the designated function; a registration information generator for, upon receiving a parameter response containing parameter specifying information specifying types of parameters necessary for generating health data corresponding to the function designated by the function designation information, prompting the user to input individual data of the user for the types of parameters specified by the received parameter specifying information and for generating registration information including the function designation information and the individual data, for storage in the storage device; and an execution requester for, upon receiving an instruction from the user for measuring a health condition, reading the registration information from the storage device and for transmitting an execution request containing the registration information to the health data generation apparatus.

The user terminal according to the present invention is capable of receiving, from a health data generation apparatus, function type information indicating the types of functions of the apparatus and causing the user to select a desired function from among the functions indicated by the function type information, and transmitting the selected function as function designation information to the health data generation apparatus. Furthermore, the user terminal causes the user to input individual data based on parameter specifying information received from the health data generation apparatus, thereby to store a pair of function designation information and individual data as registration information. Therefore, a user only has to read the registration information from the user terminal for transmission to the health data generation apparatus, to instruct the health data generation apparatus to measure a health condition with a desired function. That is, only the health data a user wishes to obtain can be generated without requiring cumbersome and complicated operations by the user. Thus, the convenience to the user is improved.

Additionally, the present invention can be implemented as a computer-readable recording medium storing a computer program (a user terminal program) for controlling a user terminal operated by a user, the user terminal capable of communicating with a health data generation apparatus having plural functions for generating plural types of health data serving as indices of health conditions, the user terminal having storage device for storing predetermined information and having a computer, the computer program at least including computer readable instructions or software code portions for causing the computer to execute: a function request process for transmitting, to the health data generation apparatus, a function request inquiring about functions of the health data device; a function designation request process for, upon receiving from the health data generation apparatus a function response containing function type information indicating types of the plural functions, displaying the functions of the health data generation apparatus based on the types of functions indicated by the function type information, the display prompting the user to designate one of the functions, and for transmitting a function designation request containing function designation information indicating the designated function; a registration information generating process for, upon receiving a parameter response containing a parameter specifying information specifying types of parameters necessary for generating health data corresponding to the function designated by the function designation information, prompting the user to input individual data of the user for the types of parameters specified by the received parameter specifying information and for generating registration information including the function designation information and the individual data, for storage in the storage device; and an execution requesting process for, upon receiving an instruction from the user for measuring a health condition, reading the registration information from the storage device and for transmitting an execution request containing the registration information to the health data generation apparatus. According to the computer-readable recording medium storing the computer program of the present invention, the same effects as described with respect to the user terminal can be attained.

BRIEF DESCRIPTION OF THE DRAWINGS

With reference to the accompanying drawings, various embodiments of the present invention will be described hereinafter.

DETAILED DESCRIPTION OF PREFERRED EMBODIMENTS

In the following, description will be given of embodiments according to the present invention with reference to the attached drawings.

A: Embodiment

Figure 1:
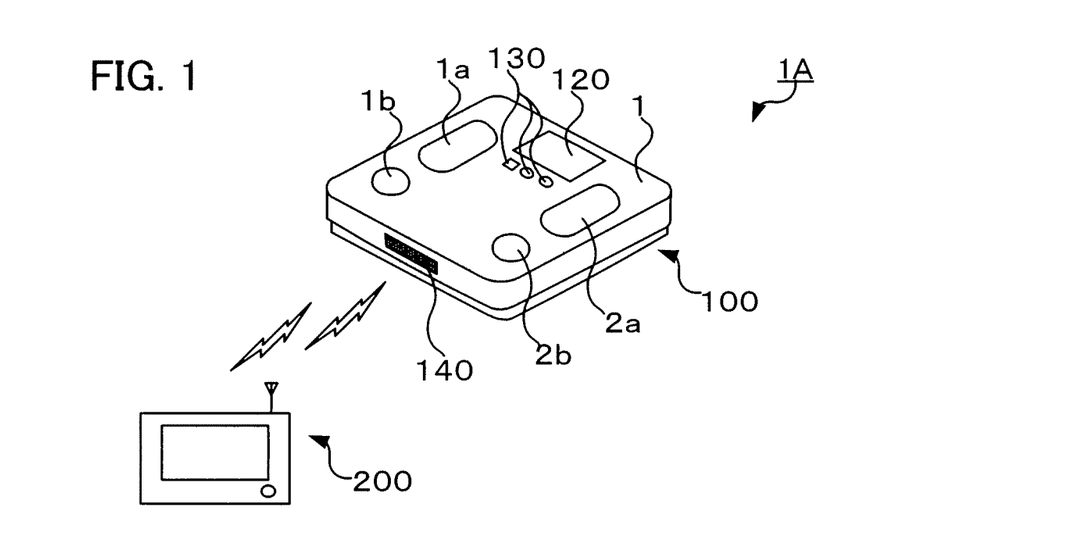
FIG. 1 is a diagram showing an overall configuration of a health data generation system.

FIG. 1 shows an overall configuration of a health data generation system 1A according to an embodiment of the present invention. As shown in FIG. 1, the health data generation system has a measuring apparatus (health data generation apparatus) 100 and a user terminal 200 capable of communicating with measuring apparatus 100. Measuring apparatus 100 is capable of measuring (i.e., generating) health data relating to a user who is a human subject, the measurement being performed based on registration information R received from user terminal 200. The registration information R of the present embodiment includes individual data and function designation information that designates one of the functions of measuring apparatus 100, such as a weight scale, a body fat percentage measuring device, and a body composition measuring device. Measuring apparatus 100, based on data contained in the individual data, performs a function designated by the function designation information. The "health data" in the present embodiment includes data of body weight, body fat, visceral fat, body water mass, bone mass, and basal metabolism that serve as indices of a health condition. The registration information R will be described later in detail.

Figure 2:
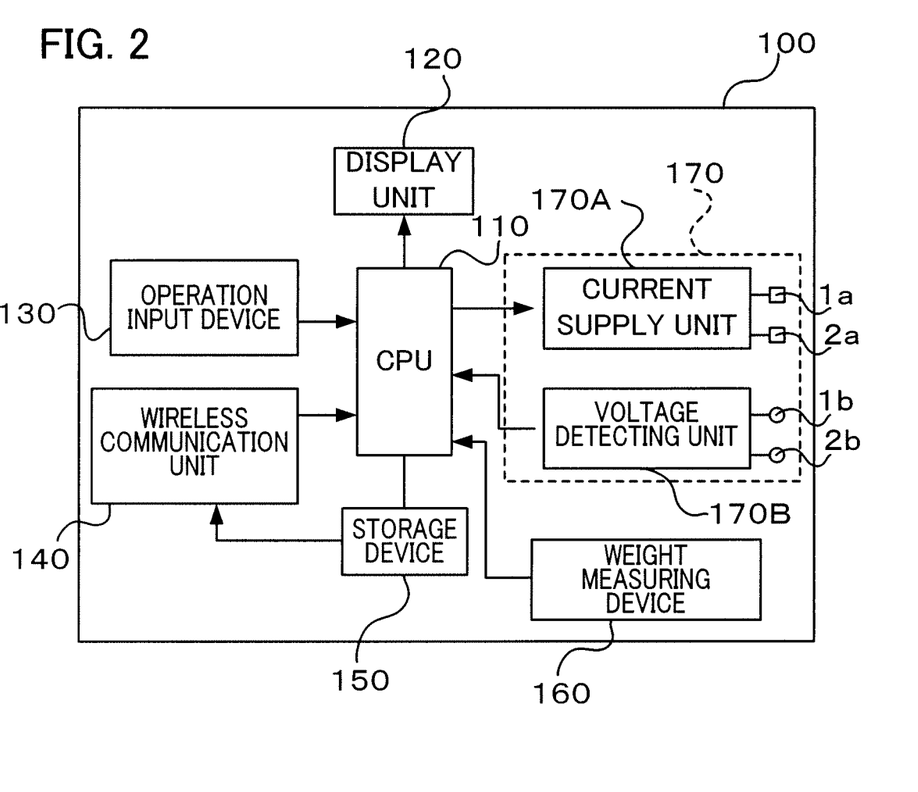
FIG. 2 is a functional block diagram showing a functional configuration of a measuring apparatus.

FIG. 2 is a functional block diagram showing a configuration of measuring apparatus 100. As shown in FIGS. 1 and 2, measuring apparatus 100 has a body 1, a display unit 120, an operation input device 130, a wireless communication unit 140, a storage device 150, and a CPU 110 that controls each of the components.

Display device 120 is a display device such as, for example, a LCD (Liquid Crystal Display), for displaying various data such as measurement data (human subject index information) measured, or health data generated by measuring apparatus 100, as well as other various data such as dates. Operation input device 130 has a menu key, an up key, and a down key, by use of which, a user of measuring apparatus 100 is able to input the characteristics of a human subject such as height, age, and sex and is also able to input various settings such as setting dates and selecting functions or selecting indices to be measured.

Wireless communication unit 140 is capable of transmitting data to, and receiving data from, user terminal 200 via a wireless communication tool, such as Bluetooth(trademark) or IrDA (Infrared Data Association (trademark)). Storage device 150 stores data input through operation input device 130 and health data generated by measuring apparatus 100, and also stores in advance a function table TBL (FIG. 3, described later), basic data such as estimation equations used for computing health data, and a computation program.

Furthermore, measuring apparatus 100 has, as a human subject index measuring device (or a measurer), a bioelectric impedance measuring device 170 (a current supply unit 170A and a voltage detecting unit 170B) and a weight measuring device 160. In a case in which a human subject steps on body 1, current supply unit 170A of bioelectric impedance measuring device 170 supplies an imperceptible constant current of a high frequency to the bottoms of the feet via electrodes 1$a$ and 2$a$ provided on the top surface of body 1, and voltage detecting unit 170B measures a potential difference via electrodes 1$b$ and 2$b$. Weight measuring device 160, when a human subject steps on body 1, measures the body weight of the human subject. Bioelectric impedance measuring device 170 and weight measuring device 160 are connected to CPU 110. CPU 110, in a case in which a weight scale is designated by the function designation information of registration information R, outputs a result of measurement supplied from weight measuring device 160 to display unit 120. In a case in which a body fat percentage measuring device or a body composition measuring device is designed by the function designation information of registration information R, computes health data in accordance with the basic data stored in storage device 150 and the characteristics of a human subject contained in the individual data of registration information R based on a result of measurement supplied from voltage detecting unit 170B and weight measuring device 160, so as to display the result of the computation as health data on display unit 120. It should be noted that measuring apparatus 100 of the present embodiment is not limited to a device such as that shown in FIG. 1 in which the bottoms of the feet of a human subject are contacted with electrodes to measure bioelectric impedance, and it may also be a device for contacting the electrodes with another part of the body of the human subject (for example, the palms). Furthermore, measuring apparatus 100 may be a known human subject index measurement device that uses other various types of measuring device to measure a condition of a human subject and to output human subject index information.

Measuring apparatus 100 of the present invention has three functions: a weighing function, a body fat percentage measuring function, and a body composition measuring function. A user operates operation input device 130, thereby selecting one of the functions, whereby measuring apparatus 100 is caused to perform the selected function. Additionally, CPU 110 of measuring apparatus 100 is capable of causing measuring apparatus 100 to perform a function designated by the function designation information contained in registration information R transmitted from user terminal 200.

In a case in which measuring device 170 is caused to function as a body fat percentage measuring device, CPU 110 estimates body fat percentage % Fat in accordance with the following equation.

$$\% \text{Fat} = f1 \cdot Z \cdot W/H^2 - f2 \qquad (1)$$

where f1 and f2 are constants that have different values depending on a sex, Z is bioelectric impedance, H is height, and W is body weight. Bioelectric impedance and body weight are measured by measuring apparatus 100. On the other hand, height is a parameter used for generating body fat percentage % FAT and is supplied from user terminal 200 as a part of the individual data of a human subject.

In the first term of Equation (1), "$W/H^2$" is body mass index, BMI, and shows the degree of obesity. The constants f1 and f2 are derived by performing a multiple regression based on a body fat percentage obtained by DXA (Dual-energy X-ray Absorptiometry). The DXA method, with the use of two types of radiation of different wavelength, determines the composition of a human body from the amounts of transmitted rays, thereby enabling a highly precise measurement of body fat percentage. However, this requires a large apparatus, and the human subject is inevitably exposed to radiation, even though the exposure is extremely small. On the other hand, the bioelectric impedance method used in the present embodiment provides a simple and secure way of estimating body fat percentage % Fat.

Figure 3:
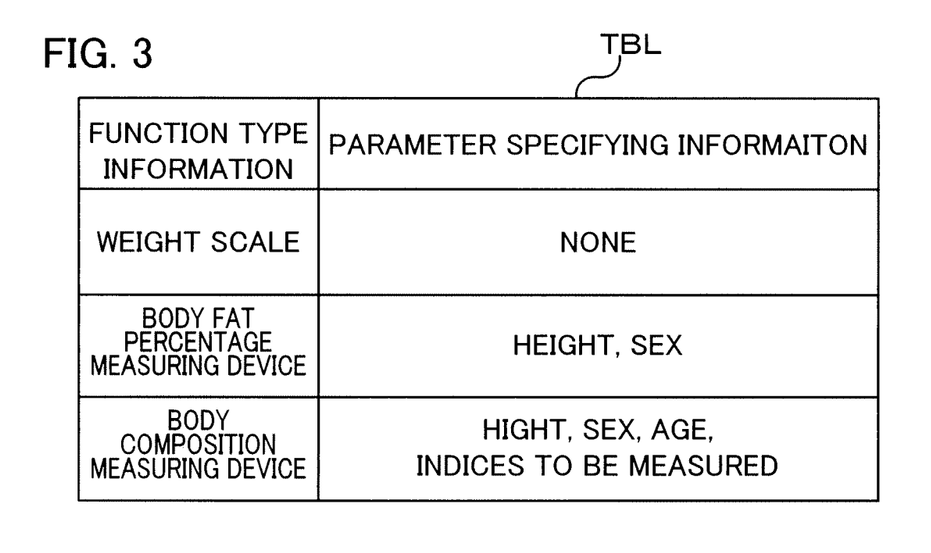
FIG. 3 is a diagram showing an example of details stored in a function table.

FIG. 3 shows an example of what is stored in a function table TBL (function information storing device) stored in storage device 150 of measuring apparatus 100. As shown in FIG. 3, in the function table TBL, three function types: a weighing function, a body fat percentage measuring function, and a body composition measuring function are stored as function type information. Furthermore, parameter specifying information is stored in association with each of the function types. The parameter specifying information specifies parameters necessary for performing each function. The parameters are indices indicating the characteristics of a human subject and include height, sex, age, and other indices that can be measured. They are used as variables in generating health data. The parameters also include the types of indices that can be measured by a particular function type. The function type information is read from the function table TBL and is transmitted to user terminal 200 in response to a request (a function inquiry) from the terminal 200. In a case in which function designation information designating a desired function selected by a user is received from user terminal 200, parameter specifying information stored in association with the function designated by the function designation information is read from the function table TBL for transmission to user terminal 200.

Figure 4:
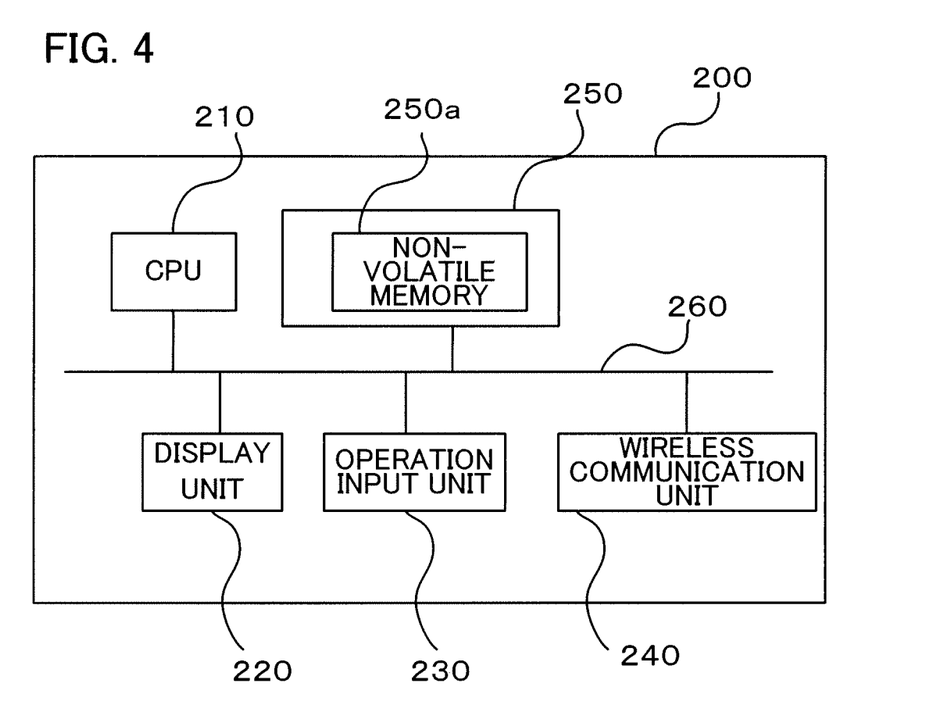
FIG. 4 is a functional block diagram showing a functional configuration of a user terminal.

FIG. 4 is a functional block diagram showing a configuration of user terminal 200. As shown in FIG. 4, user terminal 200 has a CPU 210, a display unit 220, an operation input unit 230, a wireless communication unit 240, a memory 250, and a bus 260 connecting these components. In the present embodiment, user terminal 200 is a PDA (Personal Digital Assistant). Display unit 220 is a touch-panel type LCD. Display unit 220 displays various data and receives data input from a user through the touch panel system. Operation input unit 230 has a keypad, a power button, and an enter button (none of which are shown). A user therefore is able to input data and perform setting operations by using either the touch panel or operation input unit 230.

Wireless communication unit 240 is a communication interface for performing wireless communication with an external device. In the present embodiment, wireless communication unit 240 is capable of transmitting and receiving data with measuring apparatus 100 through Bluetooth or IrDA. Furthermore, user terminal 200 is capable of connecting to the Internet (not shown) through wireless communication unit 240. Memory 250 includes a non-volatile memory 250a that stores a health data measurement program P (user terminal program), described later, and various programs such as a browser, and registration information R.

Figure 5:
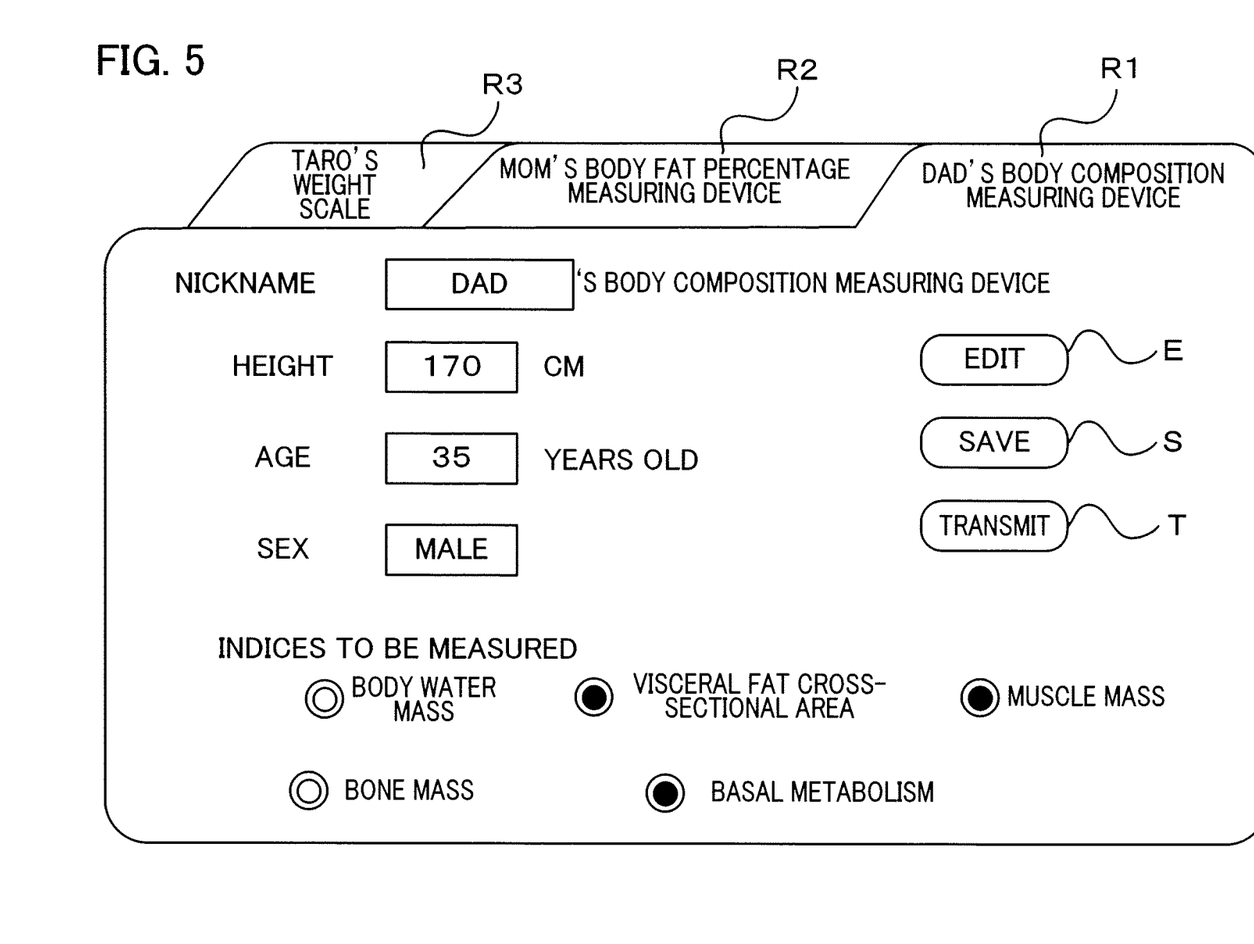
FIG. 5 is a diagram showing an example of what is displayed based on stored registration information.

FIG. 5 is a diagram showing an example of what is displayed based on registration information R that is stored in memory 250. As shown in FIG. 5, in memory 250 of user terminal 200, there are stored, as registration information R three registration information sets R1 to R3, respectively having as nicknames, "Dad's body composition measuring device", "Mom's body fat percentage measuring device", and "Taro's weight scale". As shown in the figure, the registration information set R1 contains "nickname", parameters including "height", "age", and "sex", "indices to be measured", and input information of each parameter. The input information of each parameter is stored as individual data.

The "nickname" designates a function of measuring apparatus 100 and identifies a user who is an object of measurement, i.e., a human subject. For example, the nickname "Dad's body composition measuring device" specifies the function of the measuring apparatus with "body composition measuring device". "Dad" is call name information uniquely identifying a user. In other words, the call name information is data for identifying to which user the individual data for each parameter of the registration information R belongs. Therefore, in the example shown, the individual data corresponding to the parameter fields of the registration information R1 is the individual data of "Dad". The call name is preferably a familiar or short form of a person's name or a call name used in a family, such as "Dad", "Mom", "Grandpa", "Grandma", and the like, that immediately reminds a particular person from among plural users of user terminal 200.

The body composition measuring device of the present invention is capable of measuring body water mass, visceral fat cross-sectional area, muscle mass, bone mass, and basal metabolism, from among which a user specifies one or more indices to be measured in the "indices to be measured" field.

Health data in general includes numerous types of health data such as body weight, body fat percentage, body water mass, visceral fat cross-sectional area, muscle mass, bone mass, basal metabolism, and the like. Parameters such as height, sex, and age are used for generating the health data. The number and the types of parameters required for generating the health data depend on the type of health data to be generated. Therefore, a user often has to perform complex setting and inputting operations because some functions require various settings and numerous types of information to be input by the user, the various settings including selecting which function the user wishes to use and which indices among indices that can be measured by the selected function the user wishes to measure and the numerous type of information including information on the characteristics of the user as a human subject such as height, sex, age, and the like. It is troublesome for a user if the user has to perform, for each measurement, setting and input operations depending on the type of health data the user wishes to obtain. The present embodiment is therefore configured so that the function desired by a user is readily performed at measuring apparatus 100 by registering in advance, at user terminal 200, a pair of information on a function which a user wishes to use (i.e., function designation information) and input information of the user with respect to parameters necessary for implementing the function (i.e., individual data) as registration information R and by transmitting the registration information R to measuring apparatus 100 at the time of measurement. This configuration enables a function desired by a user to be implemented without requiring complex setting and input operations by the user.

Additionally, because measuring apparatus 100 is often shared by plural users (for example, by members of a family), it is preferable that individual data for respective users be readily retrieved for use. In the conventional system, plural switches are provided on the body of a measuring apparatus so that the individual data of each user is stored in association with each switch and so that when one of the switches is turned on, health data is generated based on the individual data stored in association with the switch. In this configuration, however, a user has to remember which one of the plural switches corresponds to the individual data of the user. Therefore, an improvement in convenience has been desired. Moreover, since the number of switches that can be provided with a measuring apparatus is limited due to spatial limitations, it has been impossible to register the individual data for the number of users exceeding the number of switches.

The present embodiment is therefore configured so that each of plural sets of registration information R is assigned a nickname including function designation information and call name information uniquely identifying a user. A user is then able to specify a nickname to select a particular set of registration information R and transmit the selected registration information R to measuring apparatus 100, thereby readily enabling the implementation of a desired function at measuring apparatus 100. Specifically, by merely selecting "Dad's body composition measuring device" as a nickname, the individual data corresponding to "Dad", as a human subject, and function designation information designating a desired function, are transmitted to measuring apparatus 100. That is, a pair of individual data of a human subject and a function of measuring apparatus 100 is stored as registration information R at user terminal 200, whereby a user is relieved from complex operations of selecting a function and of inputting individual data, and a desired health data is then readily obtained.

Furthermore, in a case in which individual data of a human subject is stored at the measuring apparatus, a user other than the human subject can also access the individual data, which is not desirable. In the present embodiment, however, registration information R including individual data is stored in the memory of user terminal 200. Therefore, even in a case in which measuring apparatus 100 is shared by a number of users at a gym or a sports club and the like, desired health data can be readily obtained without individual data being seen by others.

Furthermore, since registration information R is stored in user terminal 200, which is portable, it is also possible to use the identical registration information R (i.e., the identical nickname) for plural measuring apparatuses 100 of the same type that are located remotely from one another such as one in the first floor and the other in the second floors of the user's house or one at home and the other at a sports club. Therefore, a user is no longer required to set a function and input individual data for each of such measuring apparatuses 100, and the convenience to the user is greatly enhanced.

Figure 6:
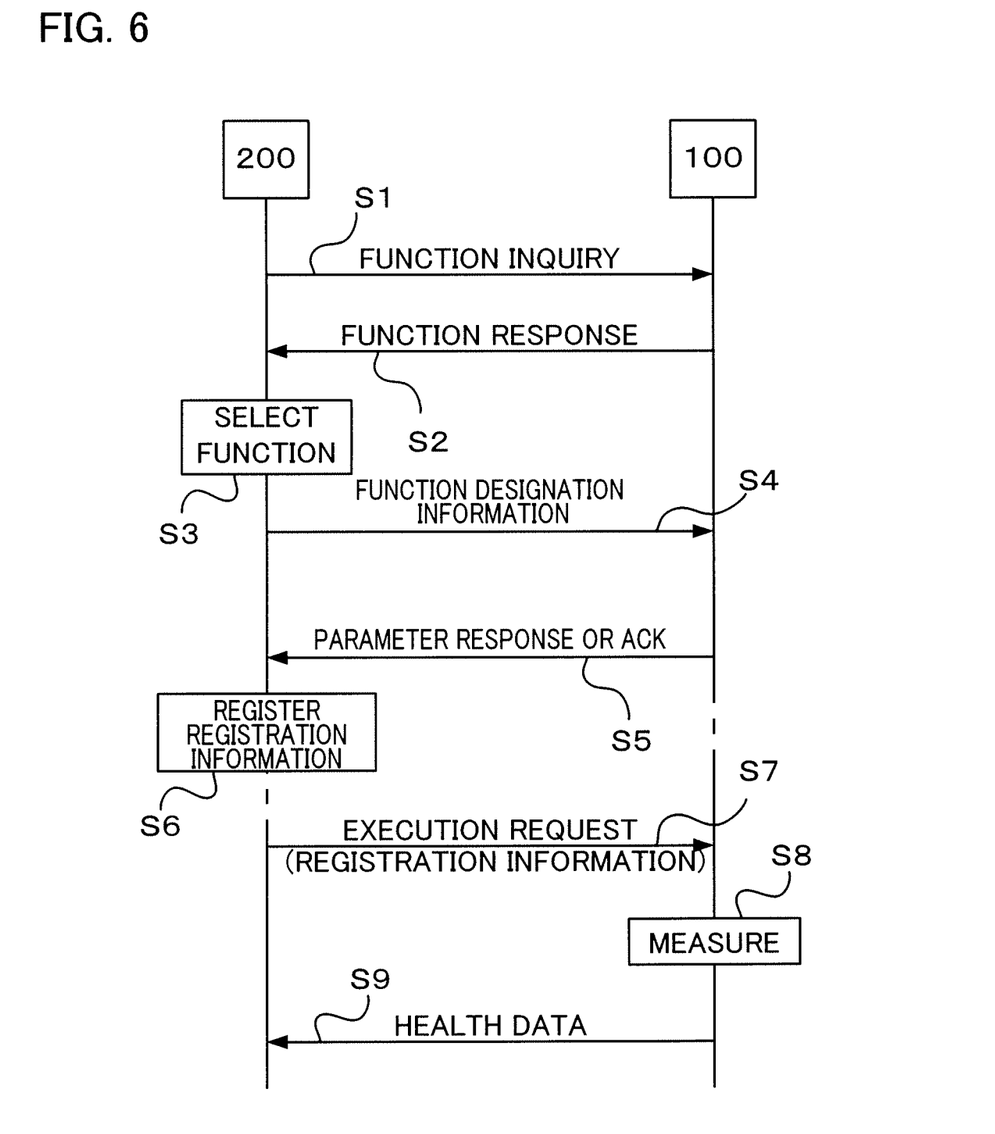
FIG. 6 is a sequence chart showing an operation of a health data generation system.
Figure 7:
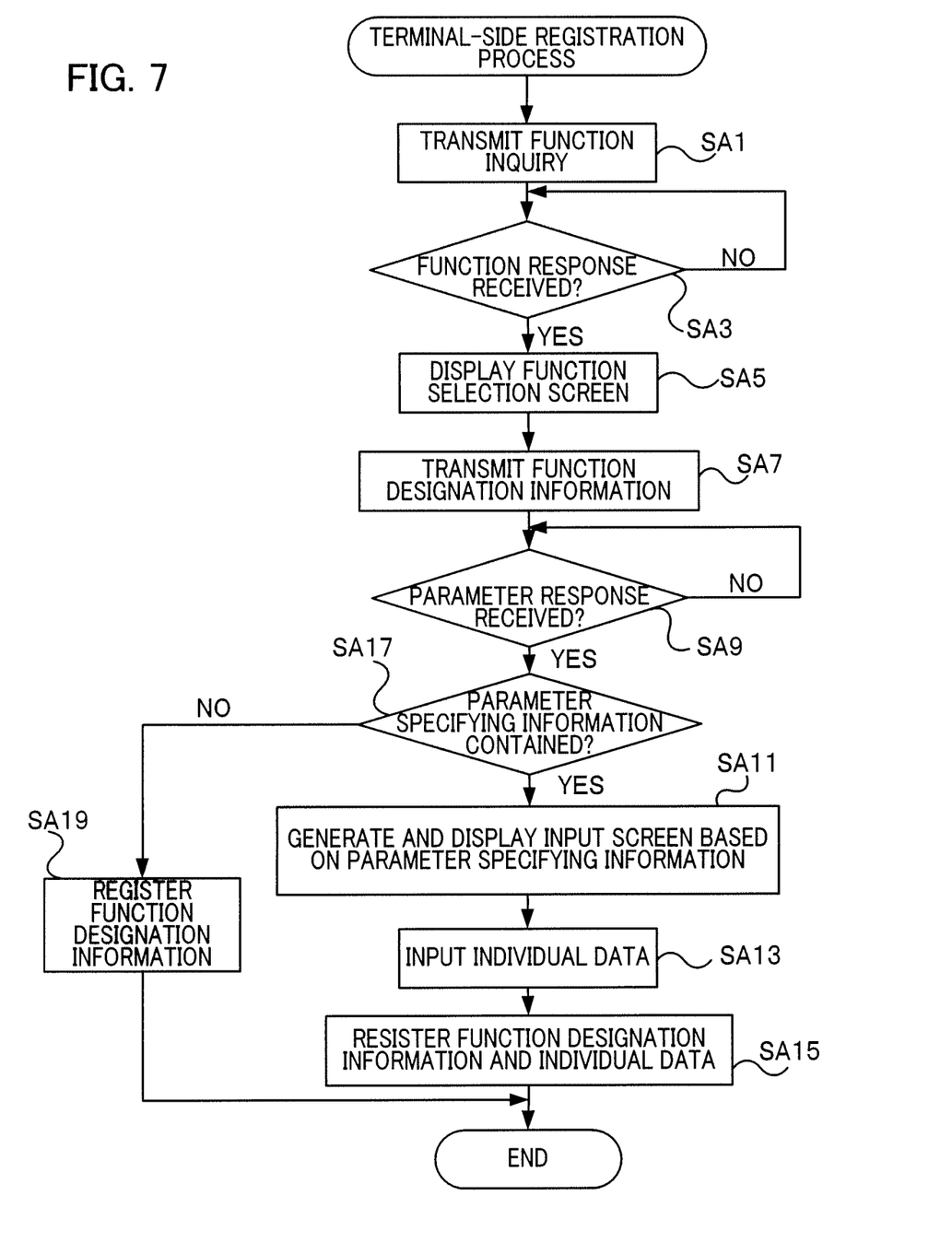
FIG. 7 is a flow chart showing a flow of a process performed at the user terminal.
Figure 8:
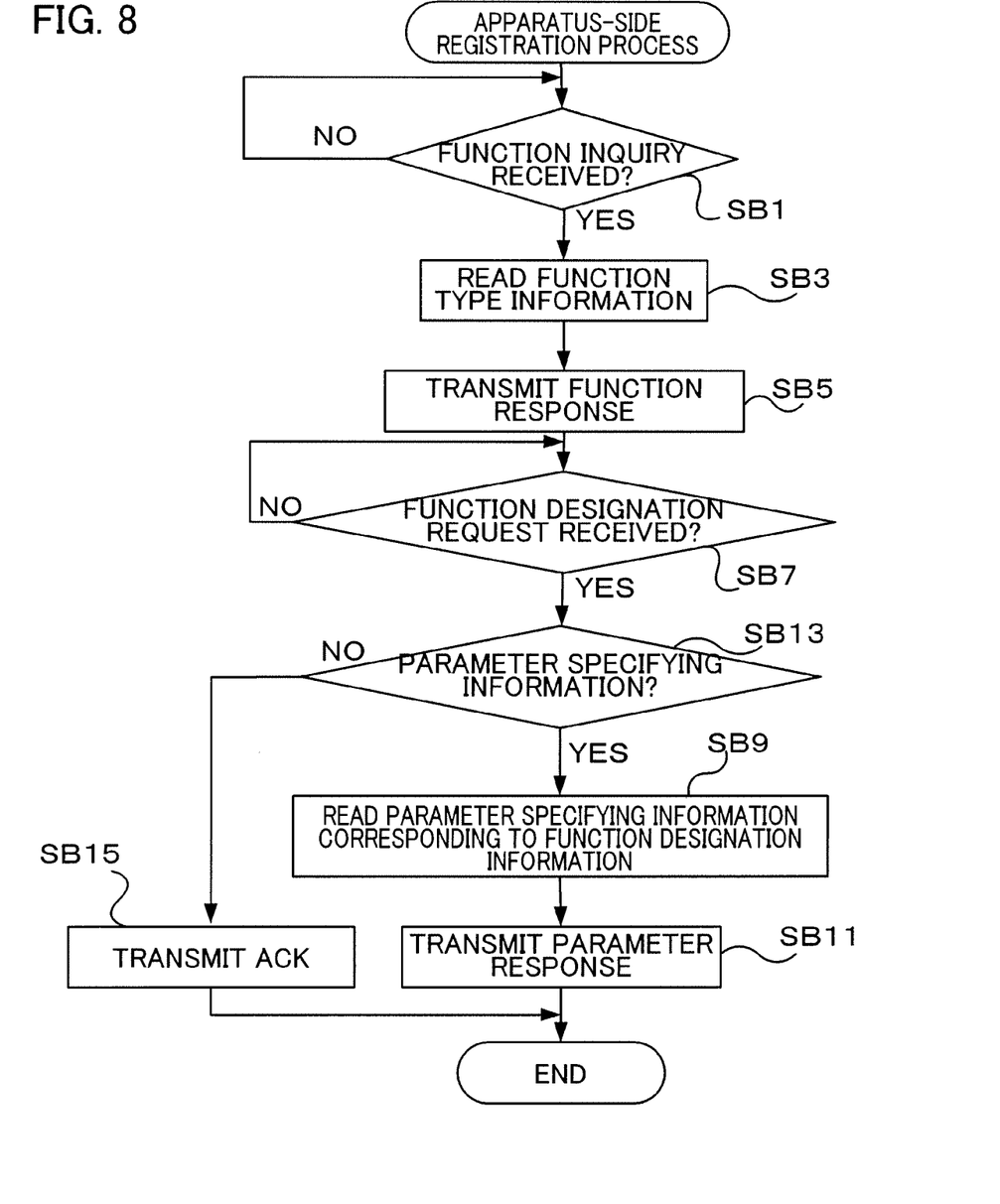
FIG. 8 is a flow chart showing a flow of a process performed at the measuring apparatus.
Figure 9A:
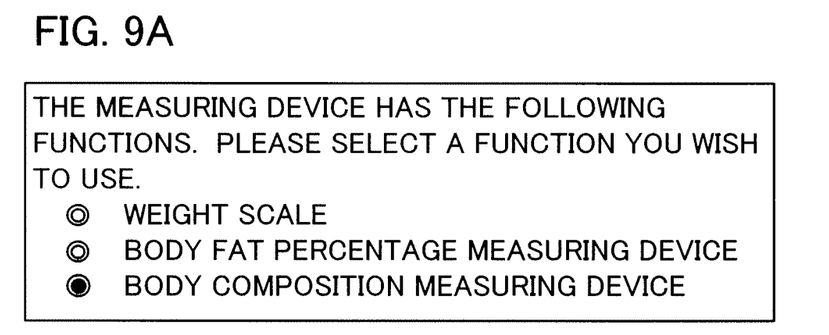
FIGS. 9A to 9C are diagrams showing examples of screens displayed in a terminal-side registration process.
Figure 9B:
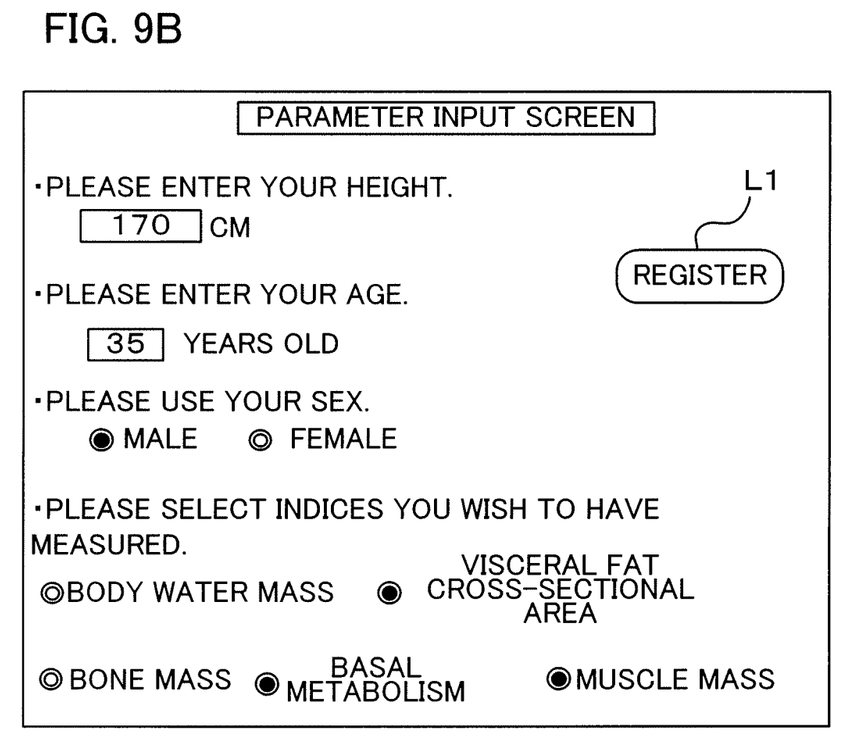
Figure 9C:
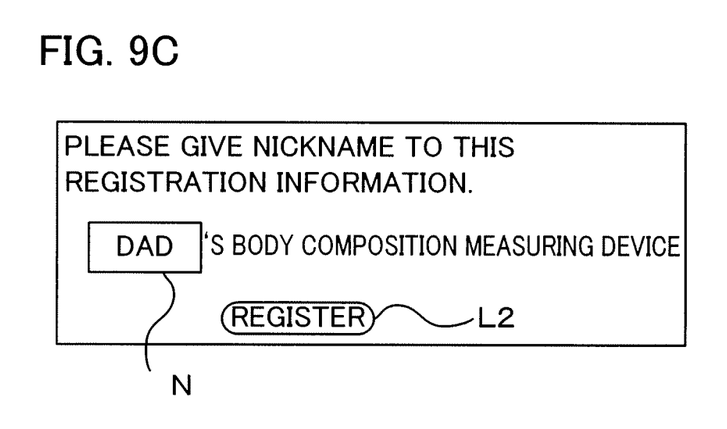

In the following, with reference to FIGS. 6 to 9C, an operation of a health data generation system 1A will be described. FIG. 6 is a sequence chart showing an operation of the health data generation system 1A. FIG. 7 is a flow chart showing a flow of a terminal-side registration process, and FIG. 8 is a flow chart showing a flow of an apparatus-side registration process. FIGS. 9A to 9C are diagrams showing examples of screens displayed in the terminal-side registration process.

In the present operational example, the health data measurement program P is stored in nonvolatile memory 250a of user terminal 200. When the health data measurement program P is activated in response to an instruction of a user, the user terminal searches a predetermined range for measuring apparatus 100. On the other hand, measuring apparatus 100 is configured so that, when a power button (not shown) of measuring apparatus 100 is pushed down, measuring apparatus 100 is switched to a mode in which the search by an external device is permitted.

CPU 210 of user terminal 200 first activates the health data measurement program P and then identifies measuring apparatus 100. CPU 210 then transmits a function inquiry to measuring apparatus 100 (Step S1, FIG. 6, and Step SA1, FIG. 7,). CPU 210 then determines whether a function response is received (Step SA3, FIG. 7). This determination is repeated until the function response is received from measuring apparatus 100 (Step SA3; NO), In the meantime, CPU 110 of measuring apparatus 100 intermittently repeats a determination of SB1 until it receives a function inquiry from user terminal 200 (Step SB1; NO, FIG. 8). When it is determined to be YES in Step SB1, CPU 110 proceeds to Step SB3, and function type information is read from the function table TBL stored in storage device 150. The function type information includes a list of three functions of measuring apparatus 100, namely, "weight scale", "body fat percentage measuring device", and "body composition measuring device" functions. CPU 110 then transmits a function response containing the read function type information to user terminal 200 (Step S2, FIG. 6 and Step SB5, FIG. 8), and it repeats the determination of Step SB7 until it receives function designation information from user terminal 200 (Step SB7; NO).

CPU 210 of user terminal 200, when it receives a function response from measuring apparatus 100 (Step SA3; YES, FIG. 7), performs a function selection process (Step S3, FIG. 6). In the function selection process, CPU 210 of user terminal 200, displays a function selection screen (FIG. 9A) based on the function type information received, to prompt the user to select a desired function (Step SA5, FIG. 7). In this example, a user selects the "body composition measuring device" function as shown in FIG. 9A. CPU 210 then transmits a function designation request to measuring apparatus 100, the function designation request containing the selected function as function designation information (Step S4, FIG. 6; Step SA7, FIG. 7). CPU 210 then repeats the determination of Step SA9 (Step SA9; NO) until it receives a parameter response from measuring apparatus 100 (Step SA9; NO).

At measuring apparatus 100, in a case in which the result of the determination of Step SB7 of FIG. 8 turns out to be YES, i.e., CPU 110 receives a function designation request containing function designation information from user terminal 200, CPU 110 refers to the function table TBL (FIG. 3), thereby determining whether there is parameter specifying information stored in association with a function designated by the received function designation information (Step SB13). In a case in which the result of the determination of Step SB13 is YES, the routine proceeds to Step SB9. In this step, CPU 110 reads from the function table TBL of storage device 150 parameter specifying information corresponding to a function designated by the received function designation information. In this operational example, the function designation information shows that the "body composition measuring device" function has been selected by the user. Therefore, CPU 110 obtains "height", "sex", "age", and "indices to be measured" from the function table TBL as parameter specifying information. CPU 110 then transmits a parameter response containing the parameter specifying information to user terminal 200 (Step S5, FIG. 6 and Step SB11, FIG. 8), and the apparatus-side registration process is then completed.

In a case in which a predetermined period has elapsed since CPU 110 has transmitted the parameter response to user terminal 200, CPU 110 automatically turns off measuring apparatus 100. That is, in a case in which an execution request (described later) is not received from user terminal 200 within a predetermined time period, communication between measuring apparatus 100 and user terminal 200 is once terminated. In a case in which user terminal 200 again communicates with measuring apparatus 100, CPU 210 again performs a process of searching for measuring apparatus 100 located within a predetermined range of distance. Preferably, the "predetermined period" is set to be longer than a time period that it would take for registration information R to be newly generated at user terminal 200 through a parameter registration process (described later), for an execution request containing the registration information R to be transmitted from user terminal 200 to measuring apparatus 100, and for the execution request to be received at measuring apparatus 100. With this configuration, user terminal 200 does not have to perform a process of searching for measuring apparatus 100 again if user terminal 200 transmits an execution request immediately after registration information R is generated, i.e., before the predetermined period elapses.

Subsequently, CPU 210 of user terminal 200, when it receives the parameter response containing parameter specifying information from measuring apparatus 100 (Step SA9; YES and Step SA17; YES, FIG. 7) executes a registration information registering process (Step S6, FIG. 6). In the process, CPU 210 displays a parameter input screen (FIG. 9B) that prompts a user to input individual data for each parameter contained in the received parameter specifying information (Step SA11, FIG. 7). In this example, input results are shown in FIG. 9B. That is, as shown in FIG. 9B, a user inputs values for "height" and "age" and selects an item from the "age" field and at least one item from the "indices to be measured" field (Step SA13). The user selects a registration button L1 upon completing the input and selection of parameters. A screen as shown in FIG. 9C is then displayed, the screen including a message that says, "please assign a nickname to this registration information" and an input box N for inputting the call name of the user. In this example, given that "body composition measuring device" has been selected by the function designation information, the "body composition measuring device" is shown to the right of the input box X in a non-editable form. When the user inputs as the call name of the user "Dad" into the input box N and then selects a registration button L2, CPU 210 registers the nickname of this registration information as "Dad's body composition measuring device" and as registration information R1 (FIG. 5) in non-volatile memory 250a together with the individual data (i.e., input information of each parameter) and function designation information (Step SA15). The terminal-side registration process is thus completed. It should be noted, in the present operational example, that there have already been stored in the non-volatile memory 250a of user terminal 200 "Mom's body fat percentage measuring device" as registration information R2 and "Taro's weight scale" as registration information R3 before the registration information R1 is generated.

In a case in which the user wishes to obtain health data immediately after the registration information R1 is registered, CPU 210 reads, from non-volatile memory 250a, registration information R1 registered as "Dad's body composition measuring device" for transmission to measuring apparatus 100 as an execution request in response to the instruction from the user to that effect. In a case in which the user wishes to obtain health data after time has passed after the registration (after measuring apparatus 100 is turned off, at the earliest), the user first turns on measuring apparatus 100 and performs an operation input at user terminal 200, the operation input for causing user terminal 200 to execute a process of searching for measuring apparatus 100. When measuring apparatus 100 is identified, the user operates operation input unit 230 of user terminal 200 or the touch panel of display device 220 to cause the screen shown in FIG. 5 to be displayed on display unit 220, so that the user is able to select desired registration information R (registration information R1 in this example) and then to select a transmission button T. CPU 210 then reads from non-volatile memory 250a registration information R1 specified by the user, for transmission to measuring apparatus 100 as an execution request (Step S7, FIG. 6).

In a case in which the user selects an edit button E when the screen of FIG. 5 is displayed on display unit 220, the stored content of the registration information R can be changed, such as that for incrementing the value set to the "age" field. The updated data is overwritten as the same registration information R upon a save button S being selected.

Subsequently, when the user (in this example, a user identified by "Dad") steps on measuring apparatus 100, the measurement is executed by the bioelectric impedance measuring device 170 and weight measuring device 160. The values obtained by the measurement (i.e., human subject index information) are then passed to CPU 110. CPU 110, based on the measured values, refers to the basic data of storage device 150 and executes the computation program to obtain health data. In this example, CPU 110 of measuring apparatus 100 performs the body composition measuring function based on the individual data of "Dad" and based on the human subject index information. Provided that, in the registration information R, visceral fat cross-sectional area, muscle mass, and basal metabolism are specified as "indices to be measured", visceral fat cross-sectional area, muscle mass, and basal metabolism are generated based on respective estimation equations and the individual data. Subsequently, measuring apparatus 100 displays each of these health data sets on display unit 120 (Step S8).

The health data generated by measuring unit 100 may be transmitted from measuring apparatus 100 to user terminal 200 (Step S9) for usage in user terminal 200 where the health data obtained from plural measurements may be monitored over time.

The above description was given for a case in which the body composition measuring function is specified. In a case in which the weighing function is specified, no individual data is required for generating health data since a result of the measurement performed by weight measuring device 160 is merely displayed on display device 120. Therefore, as shown in FIG. 3, the function type information, "weight scale", has no corresponding parameter specifying information stored in the function table TBL. In the present embodiment, measuring apparatus 100 transmits to user terminal 200 an acknowledgement message (ACK) as a response to a function specifying request (Step S5 of FIG. 6, Step SB13; NO, and Step SB15 of FIG. 8), thereby notifying user terminal 200 that there is no parameter specifying information. User terminal 200, upon receiving an ACK without parameter specifying information (Step SA17 of FIG. 7; NO), registers only the function designation information as registration information (Step SA19).

As described in the foregoing, in the health data generation system 1A according to the present embodiment, the function type information is transmitted from measuring apparatus 100 to user terminal 200, and parameter specifying information containing information on parameter types necessary for performing a function specified by the user is then transmitted from measuring apparatus 100 to user terminal 200. Therefore, the user is able to select a desired function and input necessary information (individual data) on user terminal 200. Furthermore, in the health data generation system 1A, user terminal 200 stores in its memory a pair of function designation information designating the selected function and individual data as registration information R. Therefore, the user need not specify a function or input individual data for each measurement and need only use the same registration information R repeatedly to cause measuring apparatus 100 to perform a desired function any number of times. Thus, the user is relieved from complicated setting and input operations, whereby the user convenience is enhanced.

B. Modifications

The present invention is not limited to the embodiment described above, and modifications such as those described below can be made.

(1) In the above embodiment, a PDA is used as user terminal 200: however, this is not limited thereto. A portable telephone terminal having a wireless data communication function may also be used. Furthermore, user terminal 200 is not limited to a wireless terminal, and it may be a terminal capable of transmitting and receiving data by connecting user terminal 200 and measuring apparatus 100 through a wired connection. Therefore, user terminal 200 may be immovable or be a portable personal computer. Also, registration information R generated at user terminal 200 may be carried by storing the information in a portable recording medium such as a floppy disk(trademark), a CD-ROM, and a USB memory, which then can be inserted in a drive connected to measuring apparatus 100 so as to have registration information R to be used at measuring apparatus 100.

(2) In the above embodiment, a "body composition measuring device" is treated as one function, and a user is caused to select desired indices to be measured, but each of the measurement indices may be treated as separate functions, except that the function is preferably divided so as not to make the generation of registration information cumbersome and complicated. Furthermore, in the above embodiment, the "weight scale", "body fat percentage measuring device", and "body composition measuring device" functions are used as examples of the functions of measuring apparatus 100, but the functions may be other health data measuring functions such as "visceral fat measuring device", "basal metabolism measuring device", "lower leg muscle mass measuring device", and "bone density measuring device" functions. Additionally, in the above embodiment, the types of parameters used are "height", "sex", "age", and "indices to be measured", but this is not limited thereto, and other freely selected parameters may be used. For example, "exercise amount", "amount of smoking", and "amount of drinking" per day may be used.

(3) The invention may also be implemented as a computer program, i.e., the health data measurement program P, for running on a computer system, the program at least including code portions or computer readable instructions for performing steps of a method according to the invention when run on a computer system or enabling a general purpose computer system to perform functions of the computer system according to the invention. In the above embodiment, the health data measurement program P is stored in advance in a non-volatile memory 250a of user terminal 200, but it may be provided on a data carrier, such as a floppy disk, a CD-ROM, or other types of computer-readable recording media and be stored therein as data loadable in a memory of a computer system. The data carrier may further be a data connection, such as a telephone cable or wireless connection transmitted signals representing a computer program according to the invention. For example, the health data measurement program P may be downloaded through wireless communication unit 240 by connecting to the Internet. In this case, the health data measurement program P can be easily upgraded.

(4) In the above embodiment, the health data is generated at the measuring apparatus 100, but the health data may be generated at user terminal 200. In this case, measuring apparatus 100 transmits, to user terminal 200, human subject index information obtained by measuring the conditions of a human subject such as weight and bioelectric impedance. User terminal 200 then performs a predetermined computation based on human subject index information and individual data (parameters) to generate health data. Furthermore, because the health data is generated through a predetermined computation, an estimation equation may be added or updated so as to increase the number of types of functions that can be executed in the health data generation system 1A or to update the equation to one giving more accurate estimation results.

What is claimed is:

1. A health data generation apparatus provided with plural functions of generating plural types of health data serving as indices of health conditions and to communicate with a user terminal operated by a user, the health data generation apparatus comprising:
a communication unit that communicates with a user terminal that is portable with respect to the health data generation apparatus;
a human subject index measurer that measures conditions of a human subject and outputs the measured conditions as human subject index information;
a function storage device that stores function type information indicating types of the plural functions and parameter specifying information specifying types of parameters relating to characteristics of the human subject, the parameters being used for generation of one of the plural types of health data corresponding to the one of the plural functions, wherein the plural functions generate health data including at least one of body weight, body fat percentage, visceral fat, body water mass, bone mass, and basal metabolism;
a function responder that, upon receiving, from the user terminal, via the communication unit, a function inquiry that inquires about a function of the health data generation apparatus, reads the function type information from the function storage device and transmits, via the communication unit, a function response to the user terminal, the function response containing the function type information for the plural types of functions;
a parameter responder that, upon receiving, from the user terminal via the communication unit, function designation information that designates one of the plural types of functions of the health data generation apparatus, reads, from the function storage device, the parameter specifying information corresponding to the function designated in the function designation information and transmits, via the communication unit, a parameter response containing the parameter specifying information to the user terminal;
a health data generator that, upon receiving from the user terminal, via the communication unit, an execution request containing registration information that includes the function designation information and individual data, with the execution request instructing generation of health data corresponding to the function designated by the function designation information and with the individual data corresponding to the parameter specifying information, generates the health data by executing a predetermined computation based on the human subject index information measured by the human subject index measurer and the individual data included in the registration information.

2. A health data generation apparatus according to claim 1, wherein the communication unit wirelessly communicates with the user terminal.

3. A user terminal operated by a user and to communicate with a health data generation apparatus having plural functions to generate plural types of health data serving as indices of health conditions, the user terminal comprising:
a controller;
a communication unit that communicates with an external device; and
a storage device that stores predetermined information; the controller including:
a function requester that transmits, to the health data generation apparatus, via the communication unit, a function inquiry that inquires about functions of the health data generation apparatus, wherein the functions generate health data including at least one of body weight, body fat percentage, visceral fat, body water mass, bone mass, and basal metabolism;
a function designation requester that, upon receiving from the health data generation apparatus, via the communication unit, a function response containing function type information indicating types of the plural functions, displays the functions of the health data generation apparatus based on the types of functions indicated by the function type information, the display prompting the user to designate one of the functions, and transmits a function designation request containing function designation information indicating the designated function;
a registration information generator that, upon receiving, from the health data generation apparatus, via the communication unit, a parameter response containing parameter specifying information specifying types of parameters necessary to generate health data corresponding to the function designated by the function designation information, prompts the user to input individual data of the user for only the types of parameters specified by the received parameter specifying information and generates registration information including the function designation information and the individual data, for storage in the storage device, wherein one or more sets of registration information for a particular user for each function are stored; and
an execution requester that, upon receiving an instruction from the user to measure a health condition, reads one of the one or more sets of registration information from the storage device and transmits, via the communication unit, an execution request containing the read registration information to the health data generation apparatus, wherein the user terminal is separate and remote from the health data generation apparatus.

4. A user terminal according to claim 3, wherein the user terminal wirelessly communicates with the health data generation apparatus.

5. A user terminal according to claim 3, wherein the user terminal is portable with respect to the health data generation apparatus.

6. A health data generating method for use in a health data generation system, the method comprising:

providing a first health data generation apparatus having a function storage device and a human subject index measuring device for measuring conditions of a human subject and outputting the measured conditions as human subject index information and having plural functions of generating plural types of health data serving as indices of health conditions;

providing a separate and remote user terminal in communication with the health data generation device, the user terminal having a second storage device for storing predetermined data;

storing, in the function storage device of the health data generation apparatus, function type information indicating plural types of functions and parameters specifying information specifying types of parameters relating to characteristics of the human subject, the parameters being used for generation of one of the plural types of health data corresponding to the one of the plural functions;

transmitting, from the user terminal to the first health data generation apparatus, a function inquiry for inquiring about functions of the first health data generation apparatus;

reading at the health generation apparatus, upon receiving the function inquiry, the function type information from the function storage device;

transmitting, from the first health data generation apparatus to the user terminal, a function response containing the function type information read from the function storage device;

displaying, at the user terminal, the functions of the first health data generation apparatus based on the function type information contained in the received function response, thereby prompting a user to designate one of the functions, and transmitting the designated function as function designation information to the health data generation apparatus;

reading at the health generation apparatus, upon receiving the function designation information from the user terminal, parameter specifying information specifying types of parameters necessary for generation of a type of the health data that will be generated by the function designated by the received function designation information, the parameter specifying information being read from the function storage device;

transmitting, from the first health data generation apparatus to the user terminal, the read parameter specifying information;

generating, at the user terminal, registration information including the function designation information and individual data of the user associated with each other by prompting, at the user terminal, the user to input the individual data for only the types of parameters specified by the received parameter specifying information, the registration information then being stored in the second storage device, wherein one or more sets of individual data for a particular user for each function are stored;

transmitting, from the user terminal to the first health data generation apparatus, an execution request containing registration information after reading the registration information from the second storage device in a case in which an operation input for measuring a health condition is performed by the user; and generating, at the first health data generation apparatus, upon receiving the execution request containing the registration information from the user terminal, health data corresponding to the function designated by the function designation information included in the registration information based on the human subject index information of the user and the individual data included in the registration information.

7. A health data generating method according to claim 6, wherein at least one of the plural sets of health data is generated based only on the human subject index information, wherein the step of transmitting parameter specifying information includes:

in a case in which there is parameter specifying information corresponding to the received function designation information, transmitting the corresponding parameter specifying information, and in a case in which the function designated by the function designation information generates health data based only on the human subject index information and there is no parameter specifying information corresponding to the received function designation information, notifying the user terminal; and wherein the step of registering the registration information includes the function designation information as the registration information in a case in which the user terminal receives a notification that there is no parameter specifying information corresponding to the function designation information.

8. A health data generating method according to claim 6, wherein the user terminal is used by plural users;

wherein the registration information includes function designation information, individual data of one of the plural users, and call name information for uniquely specifying the one of the plural users, wherein plural sets of function designation information and individual data exist for one call name information, and wherein the parameters included in the individual data are different for each function;

wherein the step of generating registration information includes:

prompting the user to input call name information for uniquely specifying the user; and generating a nickname representing the function designation information and the call name information and storing the nickname in association with the function designation information and with the individual data as the registration information; and wherein the step of transmitting the execution request includes:

displaying plural nicknames;

prompting the user to select one of the plural nicknames;

reading, from the storage device, as the registration information, the function designation information and the individual data corresponding to the nickname selected by the user; and transmitting the execution request containing the registration information.

9. A health data generating method according to claim 8, wherein at least one of the plural sets of health data is generated based only on the human subject index information, wherein the step of transmitting parameter specifying information includes:

in a case in which there is parameter specifying information corresponding to the received function designation information, transmitting the corresponding parameter specifying information, and in a case in which the function designated by the function designation information generates health data based only on the human subject index information and there is no parameter specifying information corresponding to the received function designation information, notifying the user terminal; and wherein the step of registering the registration information includes the function designation information as the registration information in a case in which the user terminal receives a notification that there is no parameter specifying information corresponding to the function designation information.

10. A health data generation method according to claim 6, wherein the separate and remote user terminal wirelessly communicates with the first health data generation apparatus.

11. A health data generation method according to claim 6, wherein the user terminal is portable with respect to the first health data generation apparatus.

12. A health data generation method according to claim 6, wherein the user terminal is a portable telephone terminal.

13. A health data generation method according to claim 6, wherein the user terminal is communicable at least with a second health data generation apparatus that is the same type as the first health data generation apparatus, the method further comprising:

transmitting, from the user terminal to the second health data generation apparatus, an execution request containing registration information after reading the registration information from the second storage device in a case in which an operation input to measure a health condition is performed by the user; and generating, at the second health data generation apparatus, upon receiving the execution request containing the registration information from the user terminal, health data corresponding to the function designated by the function designation information included in the registration information based on the human subject index information of the user and the individual data included in the registration information.

14. A computer-readable recording medium non-transitorily storing a computer program to control a user terminal operated by a user, the user terminal communicating with a health data generation apparatus having plural functions to generate plural types of health data serving as indices of health conditions, the user terminal having a storage device storing predetermined information, a communication unit to communicate with an external device, and having a computer, and the user terminal being separate and remote from the health data generation apparatus, the computer program at least including computer readable instructions to cause the computer to execute:

a function request process that transmits, to the health data generation apparatus, via the communication unit, a function request inquiring about functions of the health data generation apparatus, wherein the plural functions generate health data including at least one of body weight, body fat percentage, visceral fat, body water mass, bone mass, and basal metabolism;

a function designation request process that, upon receiving from the health data generation apparatus, via the communication unit, a function response containing function type information indicating types of the plural functions, displays the functions of the health data generation apparatus based on the types of functions indicated by the function type information, the display prompting the user to designate one of the functions, and that transmits a function designation request containing function designation information indicating the designated function;

a registration information generating process that, upon receiving, from the health data generation apparatus, via the communication unit, a parameter response containing parameter specifying information specifying types of parameters necessary to generate health data corresponding to the function designated by the function designation information, prompts the user to input individual data of the user for only the types of parameters specified by the received parameter specifying information and that generates registration information including the function designation information and the individual data, for storage in the storage device, wherein one or more sets of registration information for a particular user for each function are stored; and an execution requesting process that, upon receiving an instruction from the user to measure a health condition, reads one of the one or more sets of registration information from the storage device and transmits, via the communication unit, an execution request containing the read registration information to the health data generation apparatus.

* * * * *